United States Patent [19]

Wiegers

[11] Patent Number: 4,666,630
[45] Date of Patent: May 19, 1987

[54] PERFUMERY USES OF NORBORNYLBUTADIENE-ACROLEIN ADDUCTS

[75] Inventor: Wilhelmus J. Wiegers, Red Bank, N.J.

[73] Assignee: International Flavors & Fragrances Inc., New York, N.Y.

[21] Appl. No.: 850,583

[22] Filed: Apr. 11, 1986

Related U.S. Application Data

[62] Division of Ser. No. 742,537, Jun. 7, 1985, Pat. No. 4,620,039, which is a division of Ser. No. 613,568, May 24, 1984, Pat. No. 4,560,500.

[51] Int. Cl.$^4$ .......................... C11B 9/00; A61K 7/46
[52] U.S. Cl. .................................. 252/522 R; 252/8.6; 252/174.11; 252/522 A; 424/69; 424/70
[58] Field of Search ................ 252/522 R, 522 A, 8.6, 252/174.11; 424/69, 70

[56] References Cited

U.S. PATENT DOCUMENTS

| | | | |
|---|---|---|---|
| 3,499,937 | 3/1970 | Doraky et al. | 252/522 R X |
| 3,514,489 | 5/1970 | Lemberg | 568/446 |
| 3,780,109 | 12/1973 | Schleppnik | 568/445 |
| 3,812,059 | 5/1974 | Rijke et al. | 568/446 X |
| 4,014,938 | 3/1977 | Leidig | 568/445 |
| 4,076,748 | 2/1978 | Hoffmann et al. | 568/445 X |
| 4,131,557 | 12/1978 | Hall et al. | 252/522 R X |
| 4,146,505 | 3/1979 | Weber et al. | 568/445 X |
| 4,524,017 | 6/1985 | Inoue et al. | 568/445 X |
| 4,560,500 | 12/1985 | Wiegers | 252/522 R |

*Primary Examiner*—Bernard Helfin
*Attorney, Agent, or Firm*—Arthur L. Liberman

[57] ABSTRACT

Described is a genus of norbornylbutadiene-acrolein adducts defined according to the structure:

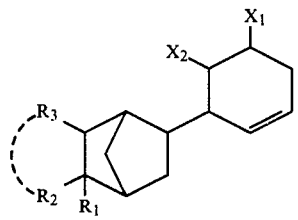

wherein one of $X_1$ or $X_2$ represents carboxaldehyde and the other of $X_1$ or $X_2$ represents hydrogen; wherein $R_1$ and $R_2$ taken together represent vinyl or ethylidene and $R_3$ represents hydrogen or $R_2$ and $R_3$ taken together completes a cyclopenteno moiety and $R_1$ represents hydrogen and uses thereof in augmenting or enhancing the aroma of consumable materials selected from the group consisting of perfume compositions, colognes and perfumed articles (e.g., perfumed polymers, solid or liquid anionic, cationic, nonionic or zwitterionic detergents, fabric softener compositions, dryer-added fabric softener articles, hair preparations, hair sprays, bath preparations and the like). Also described is a process for preparing norbornylbutadiene-acrolein adducts comprising the step of reacting the compound defined according to the structure:

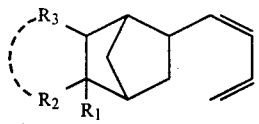

with acrolein in the presence of a Lewis acid catalyst.

8 Claims, 9 Drawing Figures

GLC PROFILE FOR EXAMPLE II.
CRUDE

GLC PROFILE FOR EXAMPLE III.
CRUDE

NMR SPECTRUM FOR FRACTION 7 OF EXAMPLE III. 2ND DISTILLATION.

IR SPECTRUM FOR FRACTION 7 OF EXAMPLE III. 2ND DISTILLATION.

PERFUMERY USES OF NORBORNYLBUTADIENE-ACROLEIN ADDUCTS

This is a divisional of application Ser. No. 742,537, filed 6/7/85 and now U.S. Pat. No. 4,620,039, issued 10/28/86, which, in turn, is a stream-line divisional of application for U.S. Pat. No. 613,568 filed 5/24/84, now U.S. Pat. No. 4,560,500 issued 12/24/85.

BACKGROUND OF THE INVENTION

The instant invention relates to the compounds defined according to the structure:

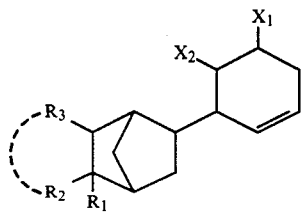

wherein one of $X_1$ or $X_2$ represents carboxaldehyde and the other of $X_1$ or $X_2$ represents hydrogen; wherein $R_1$ and $R_2$ taken together represent vinyl or ethylidene and $R_3$ represents hydrogen or $R_2$ and $R_3$ taken together completes a cyclopenteno moiety and $R_1$ represents hydrogen and the use of these compounds in augmenting or enhancing the aroma of perfume compositions, colognes and perfumed articles.

Inexpensive chemical compositions of matter which can provide earthy, seashore-like, green, woody, fruity and pineapple-like aromas with mossy, sweaty, animalic, woody, leathery and seashore-like topnotes are highly desirable in the art of perfumery. Many of the natural materials which provide such fragrances and contribute such desired nuances to perfumery compositions and perfumed articles are high in cost, unobtainable at times, vary in quality from one batch to another, have toxic properties and/or are generally subject to the usual variation of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Compositions of matter having seashore-like aromas are known in the prior art, e.g., the alkadienyl pyrazines and pyrazines as disclosed in U.S. Pat. No. 3,669,908 issued on June 13, 1972.

The structures of the chemicals set forth in U.S. Pat. No. 3,669,908 are different in kind from the structures of the chemicals of the instant case. Furthermore, the compositions of matter of the instant application are used in order to provide fragrance nuances complimentary to those provided by the seashore aromas of the compounds of U.S. Pat. No. 3,669,908 issued on June 13, 1972.

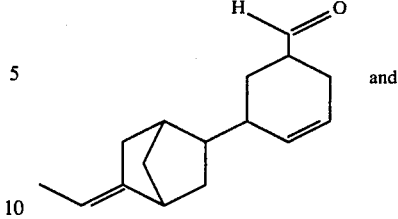

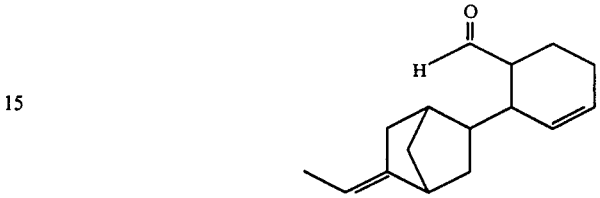

(conditions: 20% SE-30 column, 15'×0.125" programmed at 80°-250° C. at 8° C. per minute).

Figure 2:
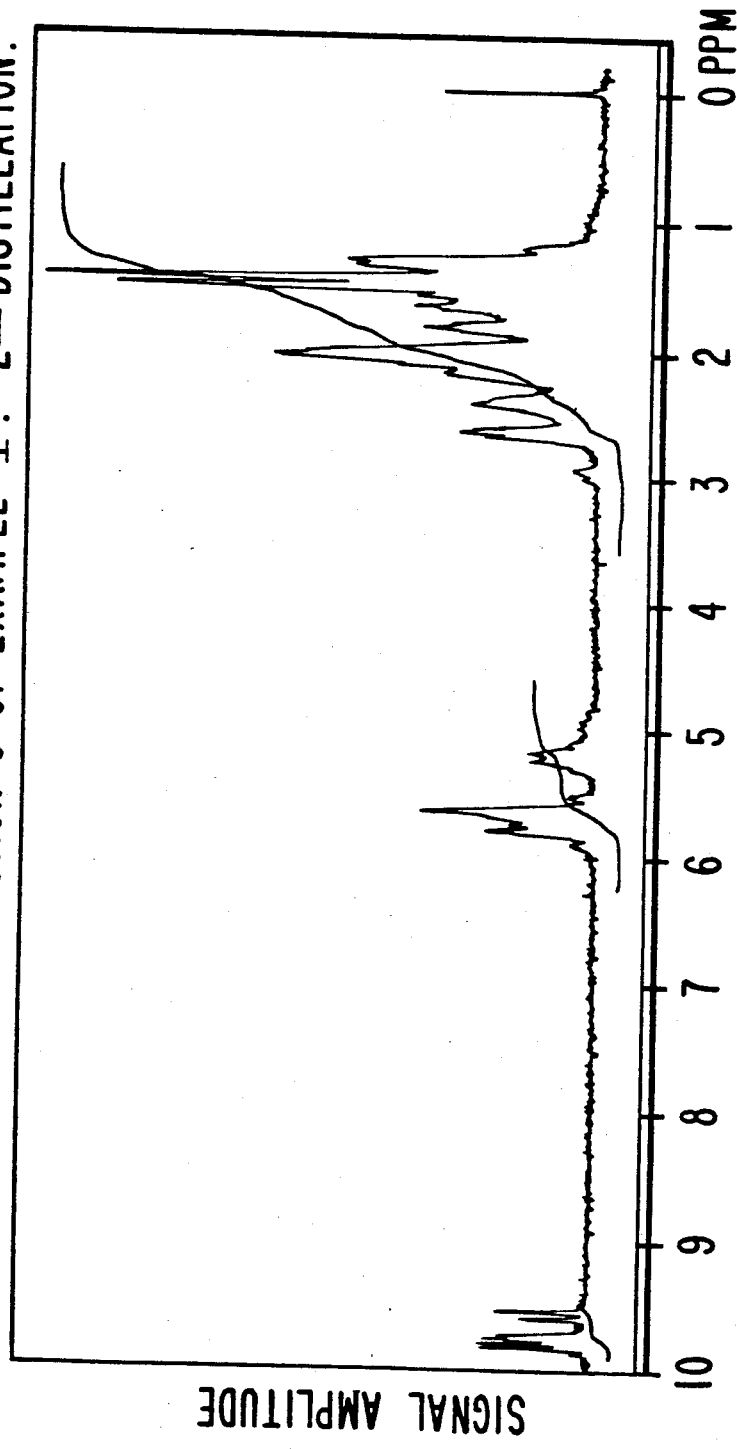

FIG. 2 is the NMR spectrum for Fraction 6 of the second distillation of the reaction product of Example I containing the compounds having the structures:

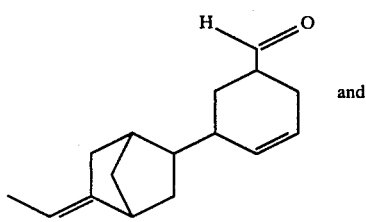

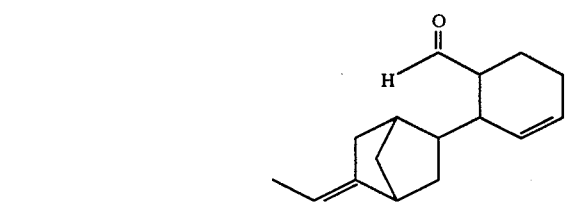

(conditions: Field strength: 100 MHz; Solvent: $CFCl_3$).

Figure 3:
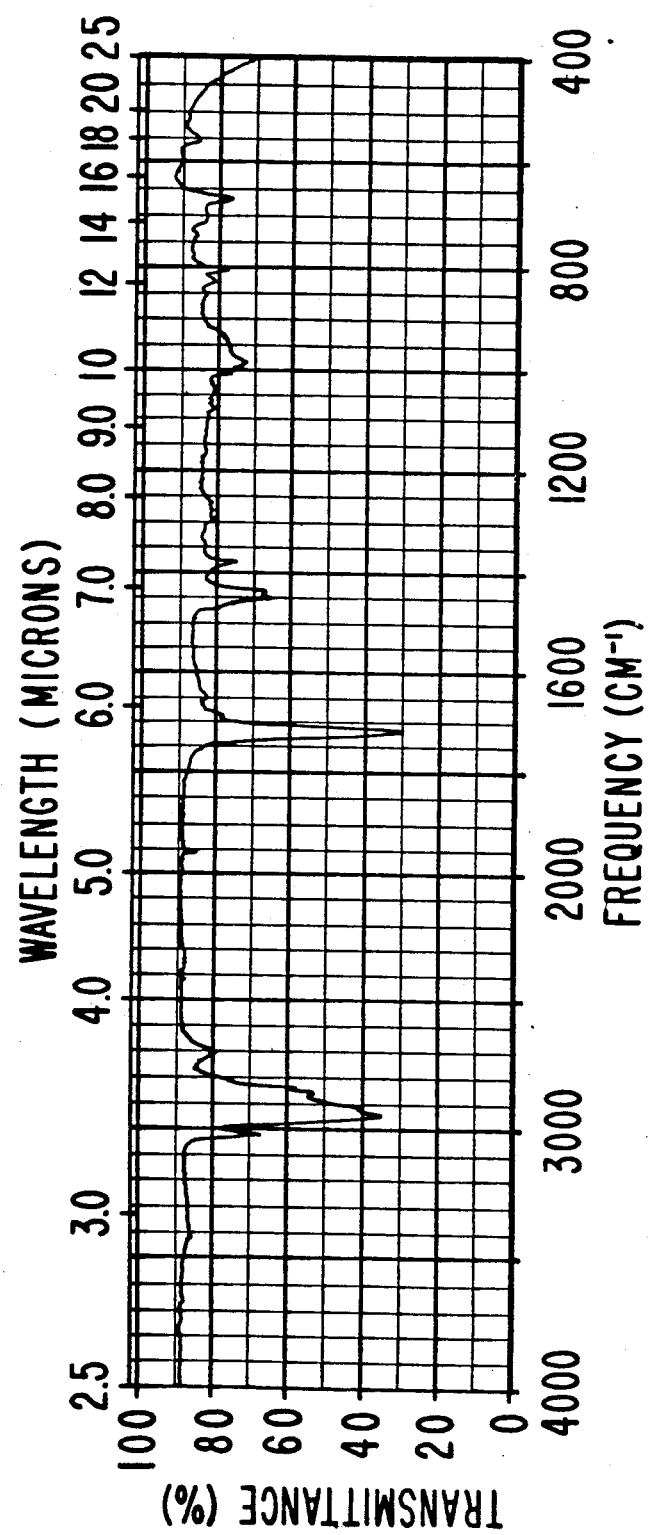

FIG. 3 is the infra-red spectrum for Fraction 6 of the second distillation of the reaction product of Example I containing the compounds having the structures:

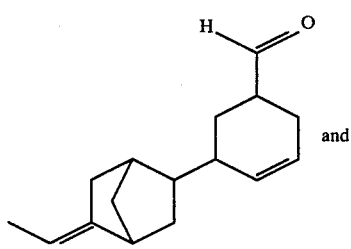

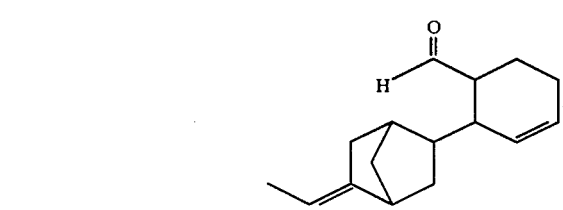

Figure 4:
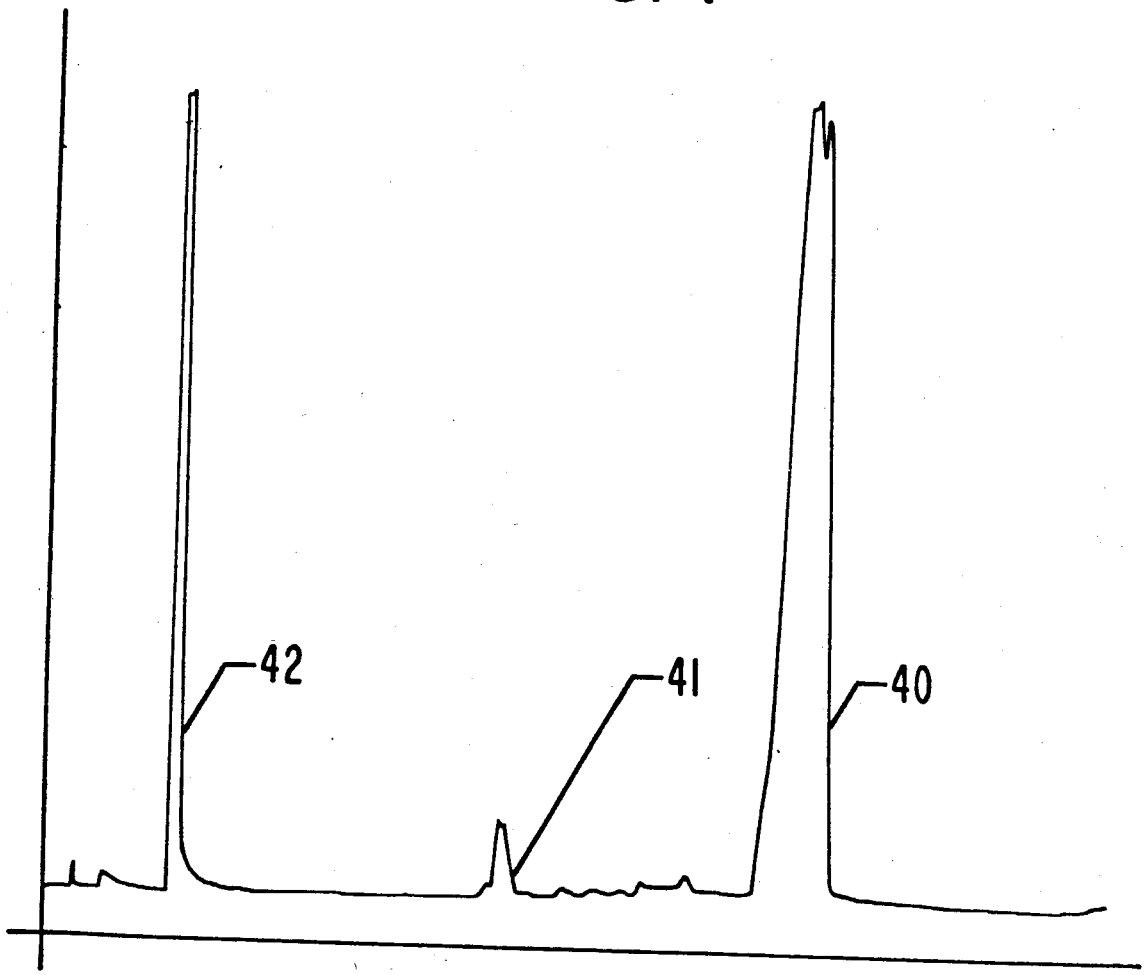

FIG. 4 is the GLC profile for the crude reaction product of Example II containing the compounds having the structures:

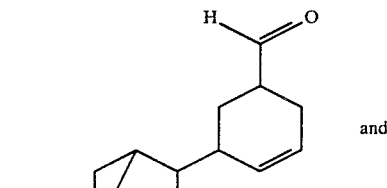

and

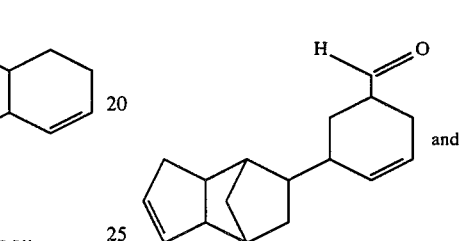

conditions: 20% SE-30 column, 15'×0.125" programmed at 80°-250° C. at 8° C. per minute).

Figure 5:
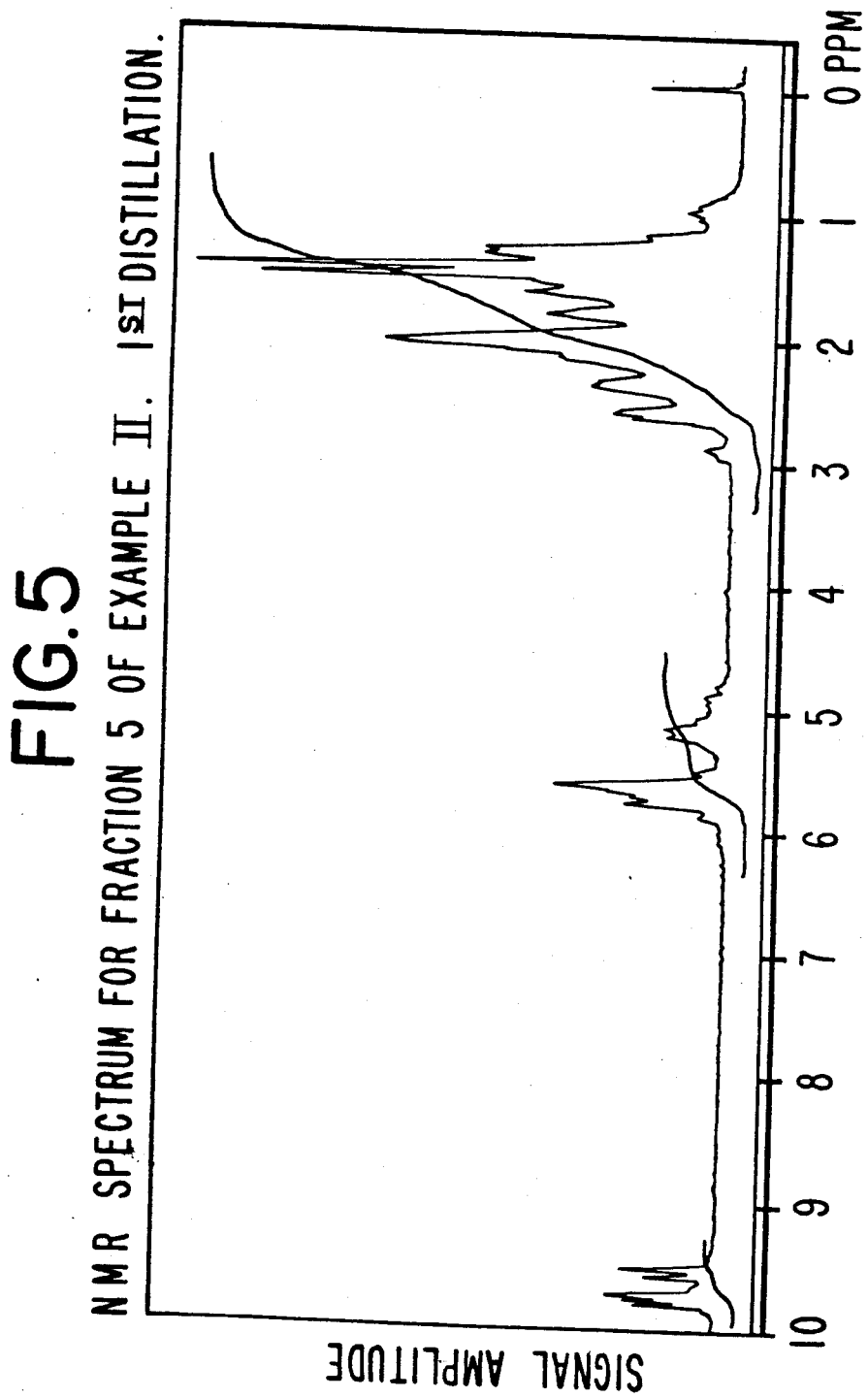

FIG. 5 is the NMR spectrum for Fraction 5 of the first distillation of the reaction product of Example II containing the compounds having the structures:

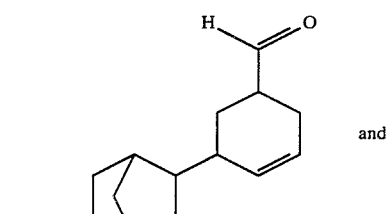

and

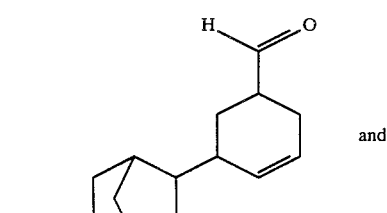

(conditions: Field strength: 100 MHz; Solvent: CFCl₃).

Figure 6:
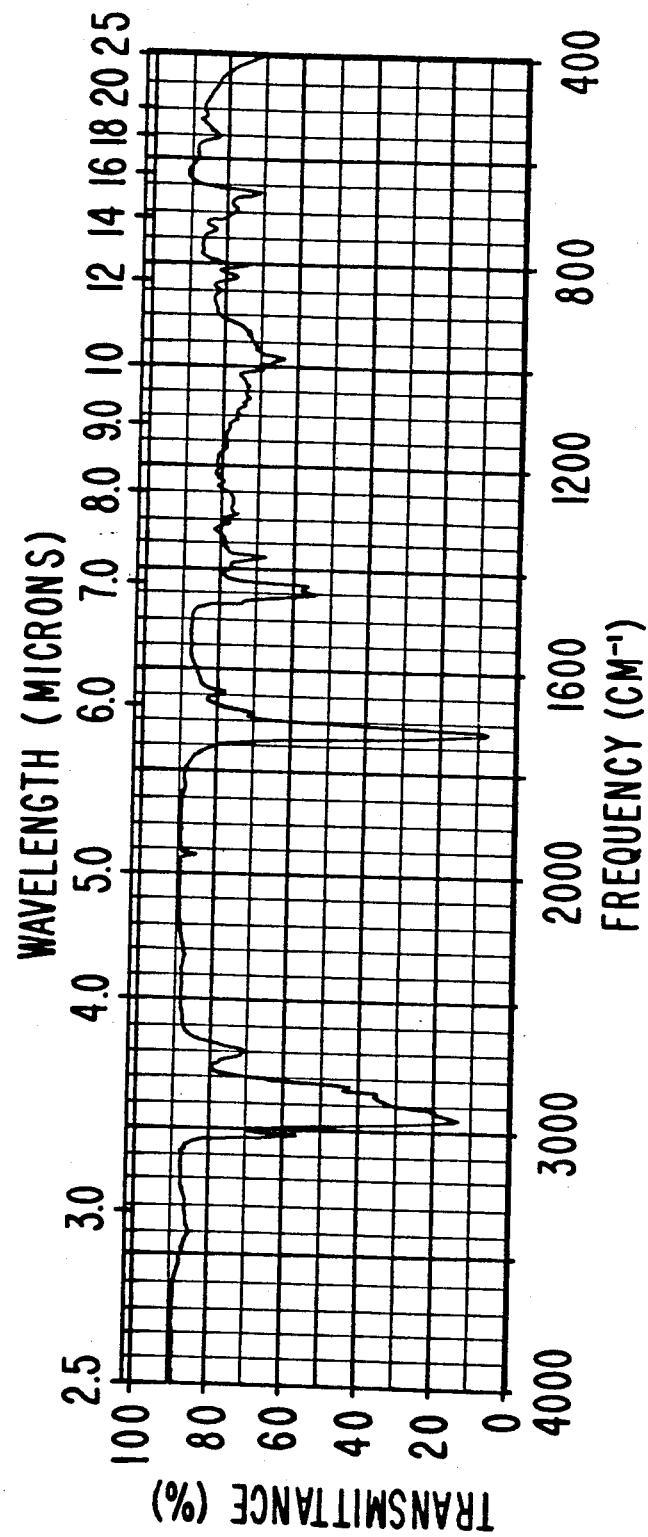

FIG. 6 is the infra-red spectrum for Fraction 5 of the first distillation of the reaction product of Example II containing the compounds having the structures:

-continued

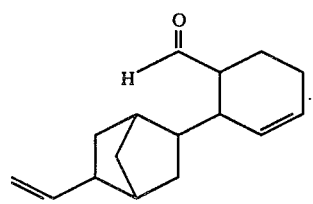

Figure 7:
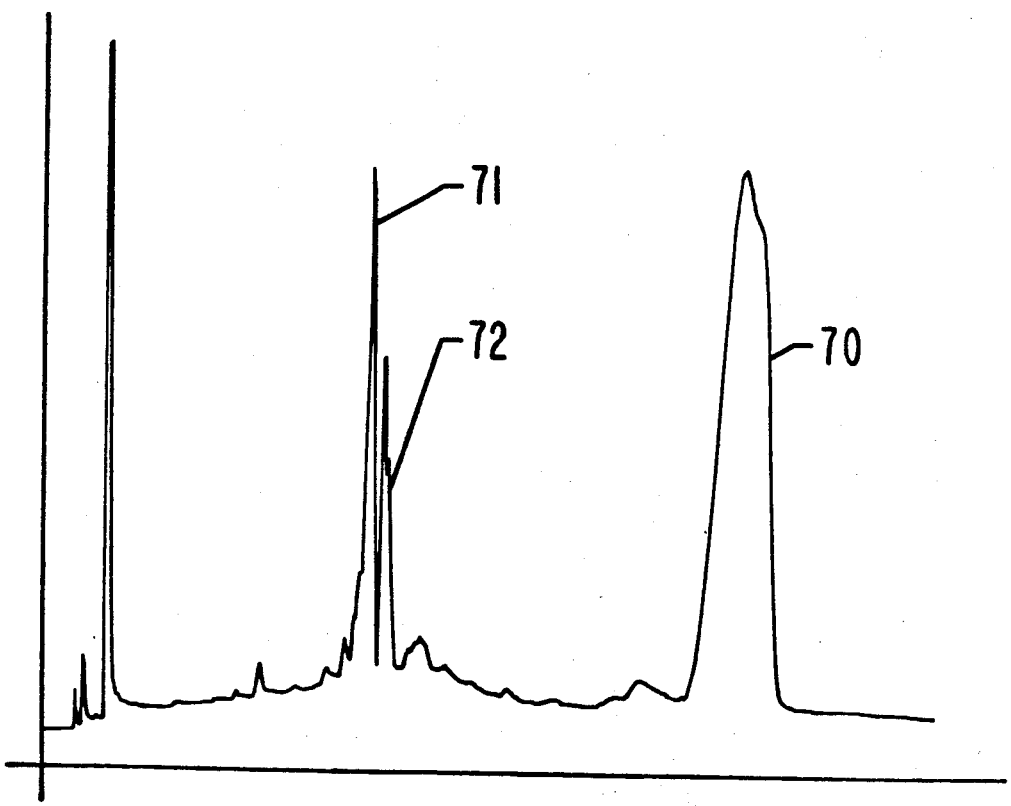

FIG. 7 is the GLC profile for the crude reaction product of Example III containing the compounds having the structures:

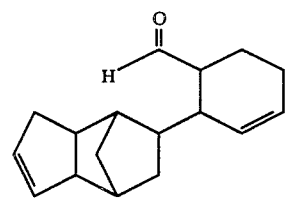

and

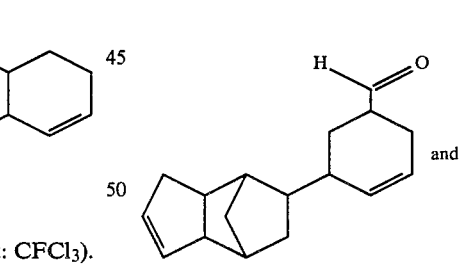

(conditions: 15'×0.125" 20% SE-30 column, programmed at 80°-150° C. at 8° C. per minute).

Figure 8:
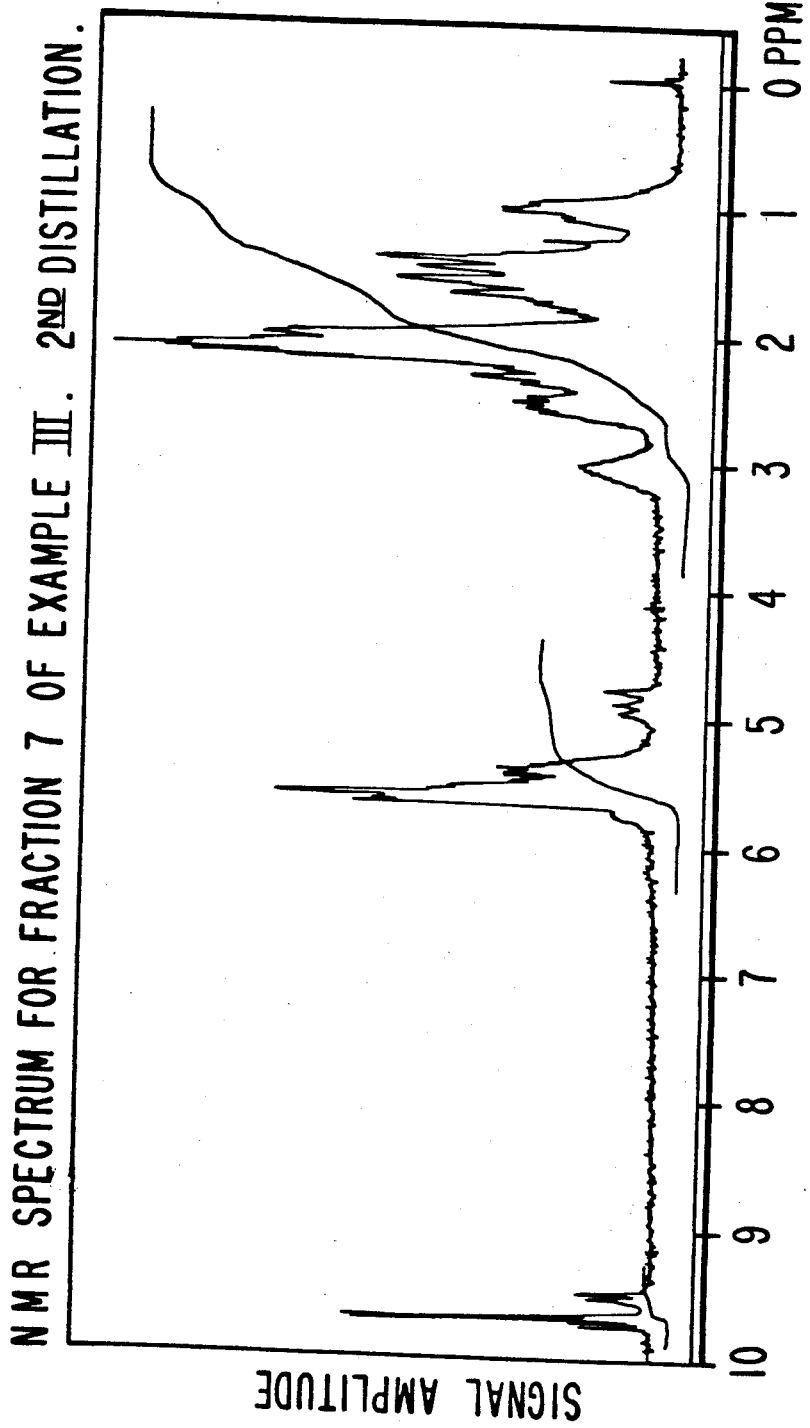

FIG. 8 is the NMR spectrum for Fraction 7 of the second distillation of the reaction product of Example III containing the compounds having the structures:

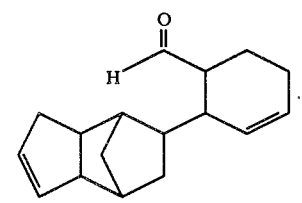

and (conditions: Field strength: 100 MHz; Solvent: CFCl₃).

Figure 9:
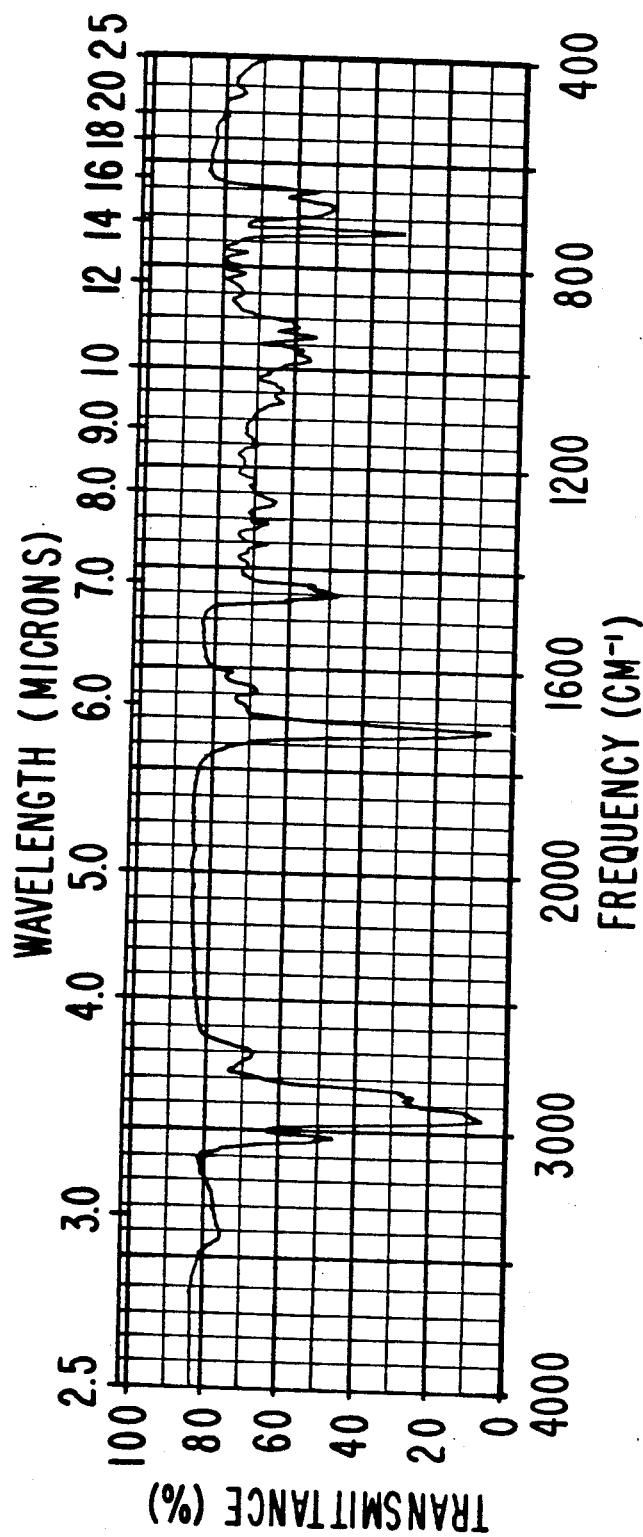

FIG. 9 is the infra-red spectrum for Fraction 7 of the second distillation of the reaction product of Example III containing the structures:

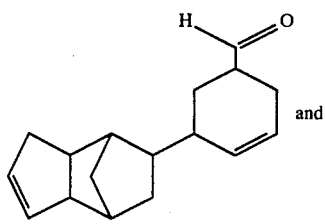

and

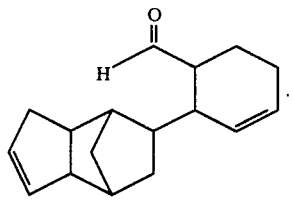

DETAILED DESCRIPTION OF THE DRAWINGS

Figure 1:
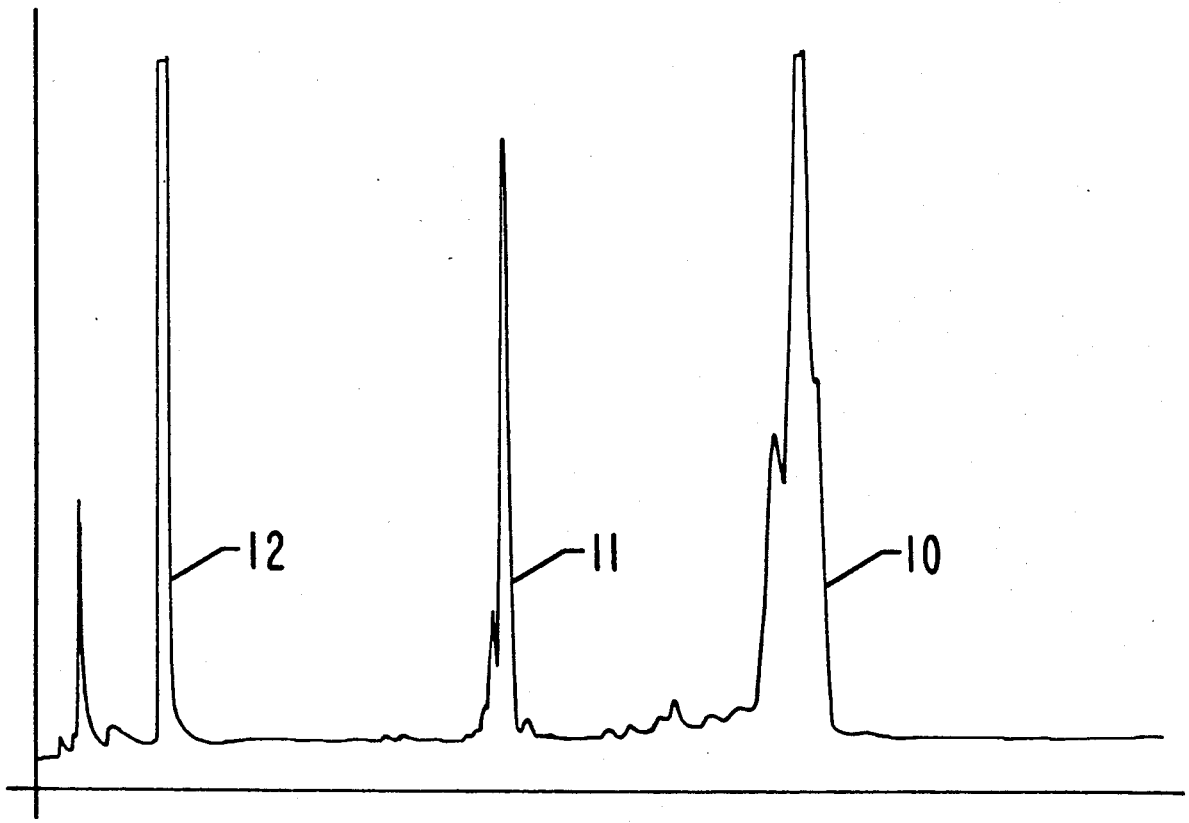
FIG. 1 is the GLC profile for the crude reaction product of Example I containing the compounds having the structures.

FIG. 1 is the GLC profile for the crude reaction product of Example I containing the compounds having the structures:

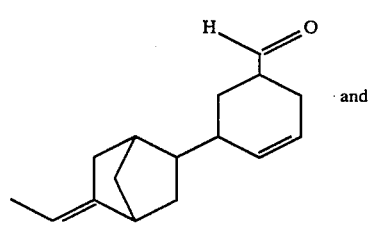

and

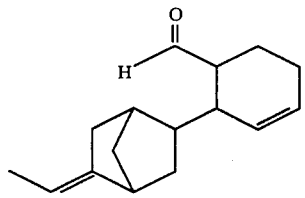

(conditions: 15'×0.125" 20% SE-30 column, programmed at 80°–250° C. at 8° C. per minute).

The peak indicated by reference numeral "10" in FIG. 1 is the peak for the products of reaction having the structures:

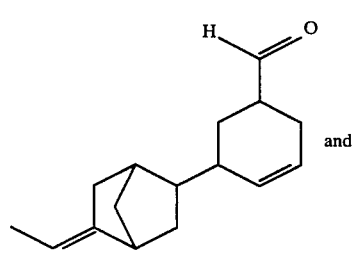

and

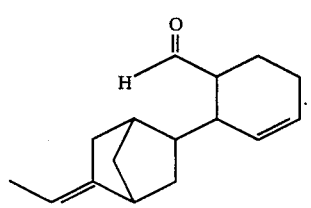

The peak indicated by reference numeral "11" is the peak for the starting material having the structure:

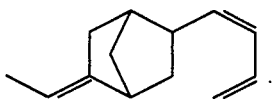

The peak indicated by reference numeral "12" is the peak for the toluene solvent.

FIG. 4 is the GLC profile for the crude reaction product of Example II containing the compounds having the structures:

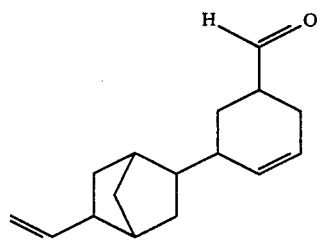

and

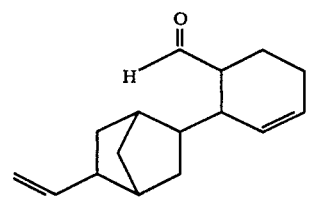

(conditions: 15'×0.125" 20% SE-30 column, programmed at 80°–250° C. at 8° C. per minute).

The peak indicated by reference numeral "40" is the peak for the reaction products having the structures:

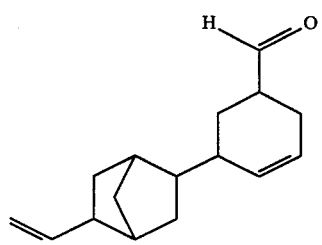

and

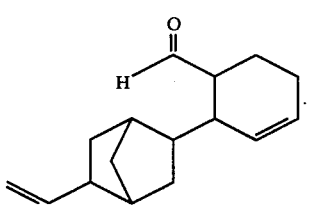

The peak indicated by reference numeral "41" is the peak for the starting material having the structure:

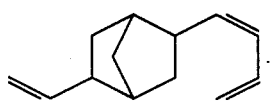

The peak indicated by reference numeral "42" is the peak for the toluene reaction solvent.

FIG. 7 is the GLC profile for the crude reaction product of Example III containing the compounds having the structures:

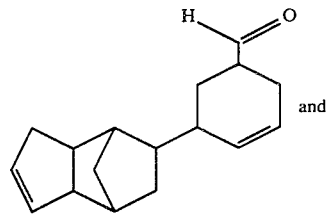
and
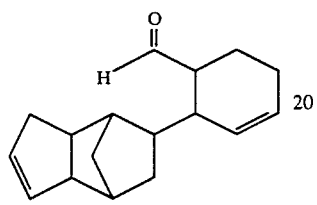

(conditions: 15"×0.125" 20% SE-30 column, programmed at 80°-250° C. at 8° C. per minute).

The peak indicated by reference numeral "70" is the peak for the reaction products having the structures:

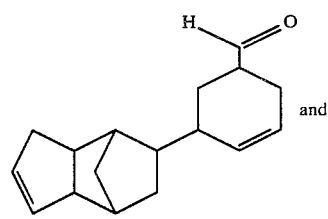
and
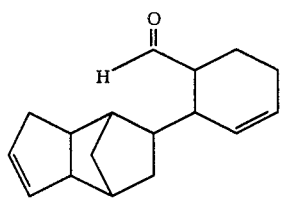

The peak indicated by reference numerals "71" and "72" is for the starting material defined according to the structure:

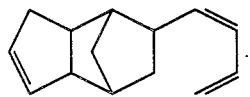

THE INVENTION

The present invention provides the norbornylbutadiene-acrolein adducts defined according to the generic structure:

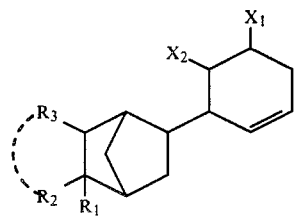

wherein one of $X_1$ or $X_2$ represents carboxaldehyde and the other of $X_1$ or $X_2$ represents hydrogen; wherein $R_1$ and $R_2$ taken together represent vinyl or ethylidene and $R_3$ represents hydrogen or $R_2$ and $R_3$ taken together completes a cyclopenteno moiety and $R_1$ represents hydrogen.

The compositions of matter of our invention produced according to the process of our invention are capable of augmenting, enhancing or providing earthy, seashore-like, green, woody, fruity, pineapple-like aromas with mossy, sweaty, animalic, woody, leathery and seashore-like topnotes in perfume compositions, colognes and perfumed articles (e.g., perfumed polymers, for example, acrylic polymers, solid or liquid anionic, cationic, nonionic or zwitterionic detergents, fabric softener articles, fabric softener compositions, dryer-added fabric softener articles, cosmetic powders, hair preparations, bath preparations, e.g., bath oils and shampoos and the like).

The substances of our invention are produced by first reacting a norbornylbutadiene derivative defined according to the structure:

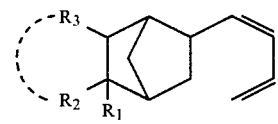

wherein $R_1$, $R_2$ and $R_3$ are defined, supra with acrolein in the presence of a Lewis acid catalyst according to the reaction:

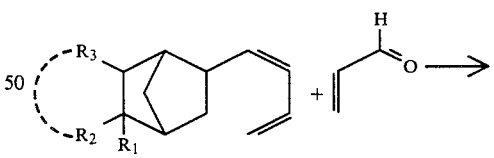

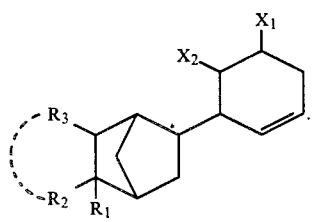

The reaction temperature may vary from about 20° C. up to about 50° C. with a preferred reaction temperature of 25°-35° C.

The mole ratio of hydrocarbon defined according to the structure:

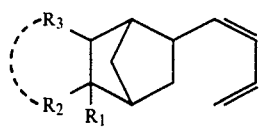

to acrolein may vary from about 1:1 up to about 1:3 with a preferred mole ratio being about 1:1.5.

Any Lewis acid catalyst is suitable, for example, stannic chloride, boron trifluoride etherate, zinc chloride or the like. The most preferred catalyst is stannic chloride pentahydrate.

The reaction takes place in the presence of a solvent which is inert to the reactants as well as to the reaction products. Examples of such inert solvents are toluene and xylene because of their relatively low volatilities.

The amount of Lewis acid catalyst in the reaction mass may vary from about 1 weight percent up to about 5 weight percent.

The time of reaction may vary from about five hours up to about twenty five hours depending upon the total desired yield of norbornylbutadiene-acrolein adducts defined according to the structure:

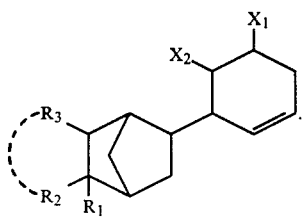

The following table sets forth examples of reaction products produced according to our invention and their organoleptic properties:

TABLE I

| Reaction Product | Organoleptic Properties |
|---|---|
| Mixture of compounds defined according to the structures: 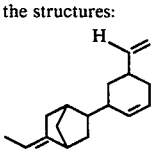 and 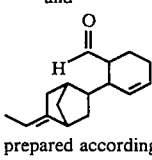 prepared according to Example I. | An earthy, seashore aroma with mossy topnotes. |
| Mixture of compounds defined according having the structures: 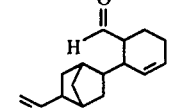 and | A green, woody aroma with sweaty, animalic topnotes. |

TABLE I-continued

| Reaction Product | Organoleptic Properties |
|---|---|
| 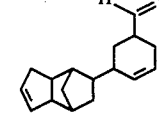 prepared according to Example II. Mixture of compounds having the structures: 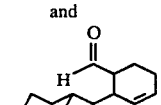 and prepared according to Example III. | A woody, fruity, pineapple-like aroma with woody leathery and seashore-like topnotes. |

One or more norbornylbutadiene-acrolein adducts prepared in accordance with the process of my invention and one or more auxiliary perfume ingredients including, for example, alcohols, ketones, aldehydes other than the aldehyde of our invention, terpenic hydrocarbons, nitriles, esters, lactones, natural essential oils and synthetic essential oils as well as ethers and thio ethers may be admixed so that the combined odors of the individual components produce a pleasant and desired fragrance particularly and preferably in the "seashore aroma" type fragrances. Such perfume compositions usually contain (a) the main note or "bouquet" or foundation stone of the composition; (b) modifiers which round off and accompany the main notes; (c) fixatives which include odorous substances which lend a particular note to the perfume throughout all states of evaporation and substances which retard evaporation; and (d) topnotes which are usually low-boiling, fresh-smelling materials.

In perfume compositions it is the individual components which contribute their particular olfactory characteristics, however, the overall sensory effect of the perfume composition will be at least the sum total of the effects of each of the ingredients. Thus, the norbornylbutadiene-acrolein adducts prepared in accordance with the process of my invention can be used to alter, modify or enhance the aroma characteristics of a perfume composition, for example, by utilizing or moderating the olfactory reaction contributed by another ingredient in the composition.

The amount of the norbornylbutadiene-acrolein adducts prepared in accordance with the process of my invention which will be effective in perfume compositions as well as in perfumed articles (e.g., perfumed polymers, anionic, cationic, nonionic or zwitterionic detergents, soaps, fabric softener compositions, fabric softener articles, bath preparations and hair preparations and the like) and colognes depends upon many factors including the other ingredients, their amounts and the effects which are desired. It has been found that perfume compositions containing as little as 0.01% of the norbornylbutadiene acrolein adducts prepared in accordance with the process of my invention or even less (e.g., 0.005%) can be used to impart earthy, seashore-like, green, woody, fruity, pineapple-like aromas with mossy, sweaty, animalic, woody, leathery and seashore-like topnotes to soaps, microporous polymers, cosmetics, anionic, cationic nonionic or zwitterionic detergents, fabric softener compositions, fabric softener articles, bath preparations, hair preparations and other products. The amount employed can range up to 70% of the fragrance components and will depend on considerations of cost, nature of the end product, tnhe effect desired in the finished product and the particular fragrance sought.

The norbornylbutadiene-acrolein adducts prepared in accordance with the process of my invention are useful (taken alone or taken together with other ingredients in perfume compositions) as (an) olfactory component(s) indetergents and soaps, space odorants and deodorants, perfumed polymers, perfumes, colognes, toilet water, bath preparations such as creams, deodorants, hand litions and sun screens, powders such as talcs, dusting powders, face powders and the like. When used as (an) olfactory component(s) as little as 0.005% of the norbornylbutadiene-acrolein adducts prepared in accordance with the process of my invention will suffice to impart earthy, seashore-like, green, woody, fruity, pineapple-like aromas with mossy, sweaty, animalic, woody, leathery and seashore-like topnotes. Generally, no more than 6% of the norbornylbutadiene acrolein adducts of my invention based on the ultimate end product is required in the perfumed article. Accordingly, the perfumed article contains a range of from about 0.005% of the norbornylbutadiene acrolein adducts up to about 6% of the norbornylbutadiene acrolein adducts based on the weight of the perfumed article.

In addition, the perfume composition or fragrance composition of my invention can contain a vehicle or carrier for the norbornylbutadiene-acrolein adducts prepared in accordance with the process of my invention. The vehicle can be a liquid such as a non-toxic alcohol (e.g., ethyl alcohol), a non-toxic glycol (e.g., 1,2-propylene glycol) or the like. The carrier can also be an absorbent solid such as a gum (e.g., gum arabic, xanthan gum or the like) or components for encapsulating the composition such as gelatin as by coacervation or such as other polymers such as an urea formaldehyde polymer for the purpose of encapsulation by means of the formation of capsules having polymeric walls.

It will thus be apparent that the norbornylbutadiene-acrolein adducts prepared in accordance with the process of my invention can be utilized to alter, modify or enhance the sensory properties particularly organoleptic properties, of a wide variety of consumable materials such as fragrance compositions, colognes and perfumed articles.

The following Examples I-III set forth means for synthesizing the products of my invention. The examples following Example III serve to illustrate the organoleptic utilities of the norbornylbutadiene-acrolein adducts of my invention.

All parts and percentages given herein are by weight unless otherwise specified.

EXAMPLE I

PREPARATION OF DIELS ALDER ADDUCT OF ETHYLIDENE NORBORNYL BUTADIENE AND ACROLEIN

Reaction:

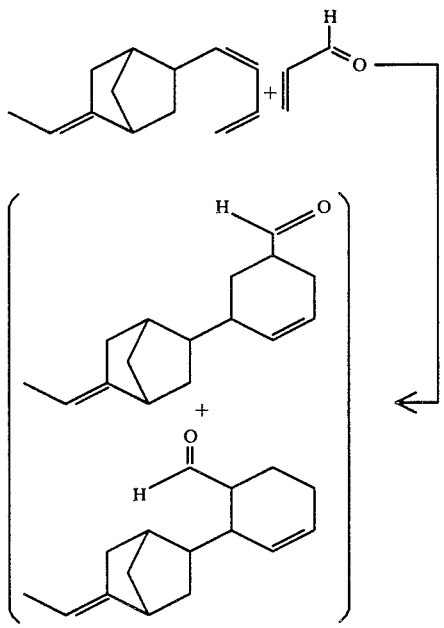

Into a 500 ml flask is placed 150 ml toluene, 5.0 grams of acetic anhydride and 4.0 grams of stannic chloride pentahydrate. The resulting mixture is stirred until dissolved at a temperature of 29° C. Over a period of two hours while maintaining the reaction mass at 20°-25° C. a mixture containing 50 grams of acrolein (0.85 moles) and 120 grams of ethylidene norbornene butadiene having the structure:

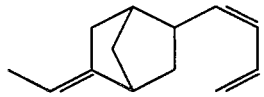

(0.69 moles) is added to the reaction mass.

Solid sodium acetate is added to the sample (4.0 grams). The reaction mass is heated to 30° C. and 10 grams of additional acrolein is added to the reaction mass followed by 0.51 grams of additional stannic chloride pentahydrate. The reaction mass is now stirred at 29°-30° C. for a period of ten hours. At the end of the ten hour period, the reaction mass is poured into a 1-liter flask containing 100 grams of concentrated hydrochloric acid and 100 grams of water. The resulting mixture is stirred for 60 minutes and cooled with crushed ice.

The organic phase is separated from the aqueous phase and, to the organic phase, 52 grams of concentrated hydrochloric acid and 50 grams of water is added. The organic phase is then washed with a 10% aqueous solution of sodium carbonate and then dried.

The resulting material is stripped of solvent and cooled and then distilled on an one plate fractionation column ("rush over distillation") yielding the following fractions:

| Fraction No. | Vapor Temp. (°C.) | Liquid Temp. (°C.) | Vacuum mm/Hg. Pressure |
|---|---|---|---|
| 1 | 27 | 102 | 5.0 |
| 2 | 93 | 165 | 2.6 |

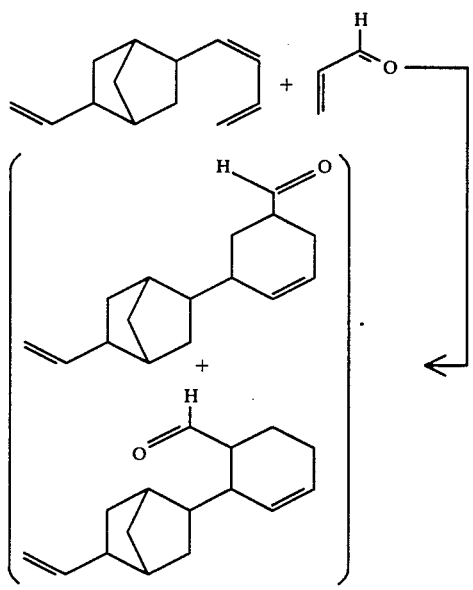

Into a 500 cc reaction vessel equipped with stirrer, thermometer, reflux condenser and heating mantle is placed 150 ml toluene, 5.8 grams of acetic anhydride and 4 grams of stannic chloride pentahydrate. The resulting mixture is stirred until dissolved. Over a period of two hours, while maintaining the reaction mass at 25°-27° C., a mixture of 60 grams acrolein and 100 grams of the compound having the structure:

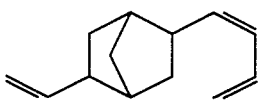

is added to the reaction mass. At the end of the addition of the acrolein and compound having the structure:

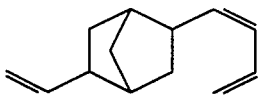

the reaction mass is stirred at room temperature for a period of 4.6 hours.

At the end of the 4.6 hour period the organic phase is separated from the aqueous phase and the organic phase is washed as follows:

1-500-ml portion of saturated sodium chloride solution;
1-500 ml portion of 10% sodium carbonate solution; and
1-500 ml portion of saturated sodium chloride solution.

The organic phase is then stripped of solvent and distilled on an one-plate "rush over" column yielding the following fractions:

| Fraction No. | Vapor Temp. (°C.) | Liquid Temp. (°C.) | Vacuum mm/Hg. Pressure |
|---|---|---|---|
| 1 | 28/25 | 40/101 | 60/50 |
| 2 | 105 | 144 | 3.0 |

-continued

| Fraction No. | Vapor Temp. (°C.) | Liquid Temp. (°C.) | Vacuum mm/Hg. Pressure |
|---|---|---|---|
| 3 | 125 | 149 | 1.9 |
| 4 | 128 | 157 | 1.9 |
| 5 | 133 | 176 | 1.9 |
| 6 | 142 | 210 | 1.9 |
| 7 | 142 | 233 | 3.4 |

Fractions 3-6 of the foregoing distillation are bulked and redistilled on an eight-plate Vigreux column yielding the following fractions:

| Fraction No. | Vapor Temp. (°C.) | Liquid Temp. (°C.) | Vacuum mm/Hg. Pressure |
|---|---|---|---|
| 1 | 110/118 | 155/157 | 2.0/2.0 |
| 2 | 129 | 158 | 1.75 |
| 3 | 124 | 158 | 1.75 |
| 4 | 125 | 159 | 1.65 |
| 5 | 125 | 159 | 1.7 |
| 6 | 125 | 159 | 1.7 |
| 7 | 128 | 161 | 1.7 |
| 8 | 125 | 171 | 1.7 |
| 9 | 124 | 174 | 1.7 |
| 10 | 126 | 177 | 1.05 |
| 11 | 125 | 185 | 1.7 |
| 12 | 128 | 198 | — |
| 13 | 127 | 123 | 2.0 |
| 14 | — | 230 | 1.5 |

FIG. 4 is the GLC profile of the crude reaction product (conditions: 15'×0.125" 20% SE-30 column, programmed at 80°-250° C. at 8° C. per minute). The peak indicated by reference numeral "40" is the peak for the compounds having the structures:

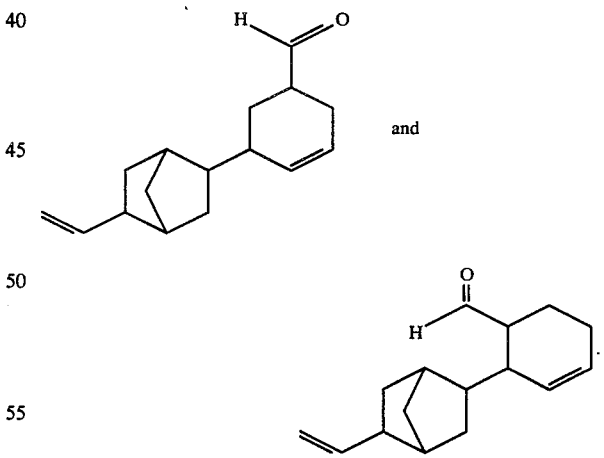

The peak indicated by reference numeral "41" is the peak for the starting material having the structure:

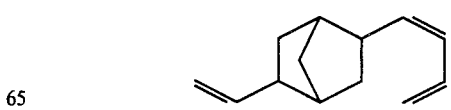

The peak indicated by reference numeral "42" is the peak for the reaction solvent, toluene.

-continued

| Fraction No. | Vapor Temp. (°C.) | Liquid Temp. (°C.) | Vacuum mm/Hg. Pressure |
|---|---|---|---|
| 3 | 137 | 176 | 3.7 |
| 4 | 141 | 202 | 3.0 |
| 5 | 149 | 229 | 3.4 |
| 6 | 141 | 260 | 2.1 |

Fractions 3–6 are bulked and redistilled on an eight-plate Vigreux column yielding the following fractions:

| Fraction No. | Vapor Temp. (°C.) | Liquid Temp. (°C.) | Vacuum mm/Hg. Pressure |
|---|---|---|---|
| 1 | 85 | 137 | 1.9 |
| 2 | 122 | 152 | 1.9 |
| 3 | 125 | 155 | 1.9 |
| 4 | 127 | 156 | 1.8 |
| 5 | 127 | 158 | 1.8 |
| 6 | 127 | 158 | 1.8 |
| 7 | 128 | 165 | 1.8 |
| 8 | 122 | 175 | 1.8 |
| 9 | 120 | 220 | 1.8 |

FIG. 1 is the GLC profile of the crude reaction product. The peak indicated by reference numeral "10" is the peak for the products defined according to the structures:

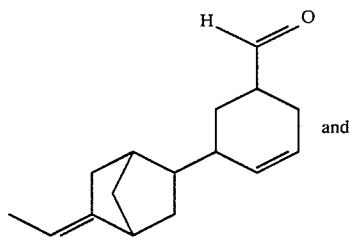
and

The peak indicated by reference numberal "11" is the peak for the starting material having the structure:

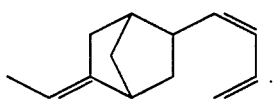

The peak indicated by reference numeral "12" is the peak for the reaction solvent, toluene.

FIG. 2 is the NMR spectrum for Fraction 6 of the second distillation containing the compounds having the structures:

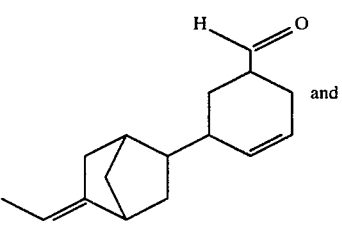
and
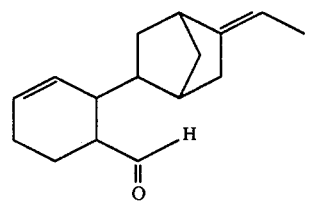

(conditions: Field strength: 100 MHz; Solvent: CFCl₃).

FIG. 3 is the infra-red spectrum for Fraction 6 of the second distillation containing the compounds having the structures:

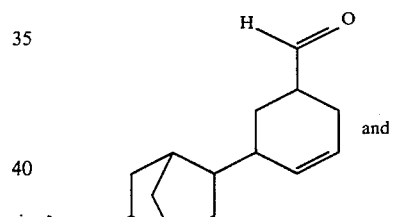
and
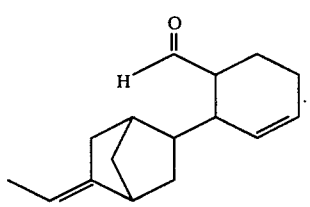

Bulked Fractions 5–7 of the second distillation have an earthy, seashore-like aroma with mossy topnotes.

EXAMPLE II

PREPARATION OF THE REACTION PRODUCT OF VINYL NORBORNYL BUTADIENE AND ACROLEIN

Reaction:

FIG. 5 is the NMR spectrum for Fraction 5 of the first distillation containing the compounds having the structures:

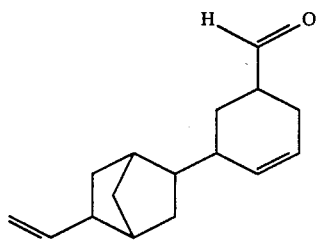

and

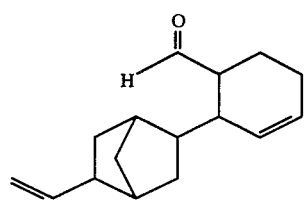

(conditions: Field strength: 100 MHz; Solvent: CFCl₃).

FIG. 6 is the infra-red spectrum for Fraction 5 of the first distillation containing the compounds having the structures:

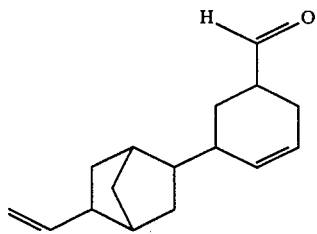

and

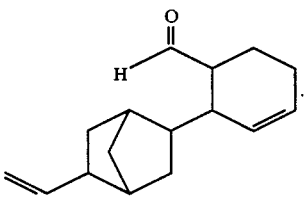

Bulked Fractions 5-10 of the foregoing second distillation containing the compounds having the structures:

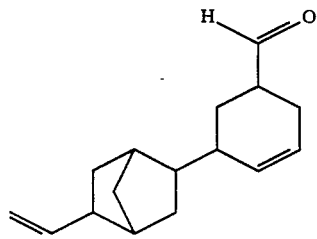

and

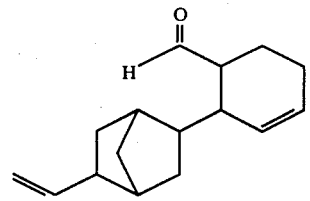

have a green, woody aroma with sweaty and animalic topnotes.

EXAMPLE III

REACTION PRODUCT OF CYCLOPENTENONORBORNYL BUTADIENE AND ACROLEIN

Reaction:

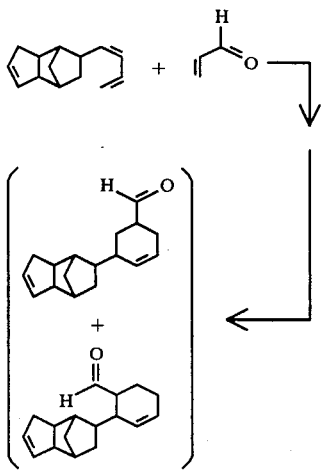

Into a 1-liter reaction flask equipped with stirrer, thermometer, addition funnel and reflux condenser and heating mantle, under a nitrogen blanket is placed 150 ml toluene and 5 grams of stannic chloride pentahydrate. The stannic chloride pentahydrate is dissolved by heating. The resulting mixture is cooled to 35° C. and over a five hour period while maintaining the reaction mass at 35°-37° C., a mixture of 200 grams of the compound having the-structure:

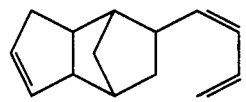

and 85 grams of acrolein is added to the reaction mass.

The reaction mass is stirred for a period of five hours while maintaining same at 25°-35° C. At the end of the five hour period, 250 grams of a 10% hydrochloric acid solution is added while keeping the reaction mass cooled at 30° C. The reaction mass is then stirred at 30° C. for a 30 minute period.

The organic phase is separated from the aqueous phase and the organic phase is then distilled on a 12" Vigreux column yielding the following fractions:

| Fraction No. | Vapor Temp. (°C.) | Liquid Temp. (°C.) | Vacuum mm/Hg. Pressure |
|---|---|---|---|
| 1 | 50/ | 100/ | 1.4 |
| 2 | 91 | 137 | 3.1 |
| 3 | 105 | 154 | 3.1 |
| 4 | 136 | 165 | 2.6 |
| 5 | 142 | 170 | 2.2 |
| 6 | 145 | 193 | 2.8 |
| 7 | 154 | 230 | 4.0 |
| 8 | 155 | 230 | 2.7 |

Fractions 4–7 are bulked and the resulting product is then redistilled on an eight-plate Vigreux column yeilding the following fractions:

| Fraction No. | Vapor Temp. (°C.) | Liquid Temp. (°C.) | Vacuum mm/Hg. Pressure |
|---|---|---|---|
| 1 | 102 | 158 | 1.55 |
| 2 | 123 | 163 | 1.55 |
| 3 | 123 | 163 | 1.55 |
| 4 | 124 | 162 | 1.5 |
| 5 | 124 | 163 | 1.4 |
| 6 | 124 | 103 | 1.4 |
| 7 | 124 | 163 | 1.4 |
| 8 | 124 | 163 | 1.4 |
| 9 | 124 | 165 | 1.4 |
| 10 | 127 | 175 | 1.4 |
| 11 | 120 | 185 | 1.4 |
| 12 | 130 | 220 | 1.4 |

FIG. 7 is the GLC profile for the crude reaction product containing the compound having the structure:

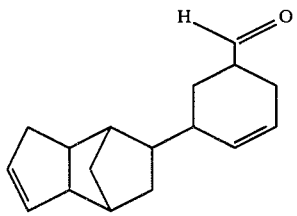

and the compound having the structure:

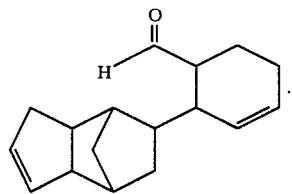

The peak indicated by reference numeral "70" is the peak for the compounds having the structures:

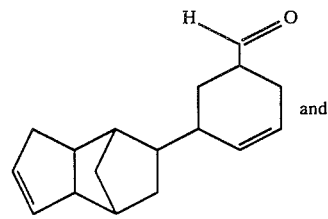

and

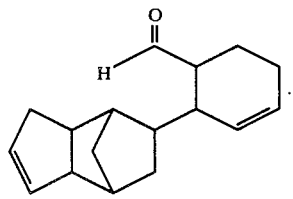

The peak indicated by reference numerals "71" and "72" are the peaks for the starting material having the structure:

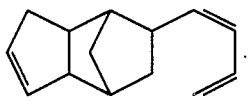

The conditions for the GLC analysis are: 15'×0.125" 20% SE-30 column, programmed at 80°–250° C. at 8° C. per minute.

FIG. 8 is the NMR spectrum for Fraction 7 of the second distillation containing the compounds having the structures:

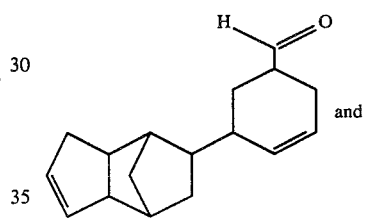

and

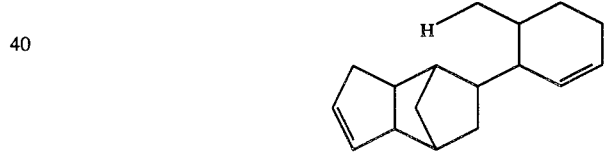

(conditions: Field strength: 100 MHz; Solvent: CFCl$_3$).

FIG. 9 is the infra-red spectrum for Fraction 7 of the foregoing second distillation containing the compounds having the structures:

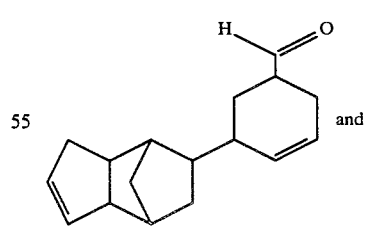

and

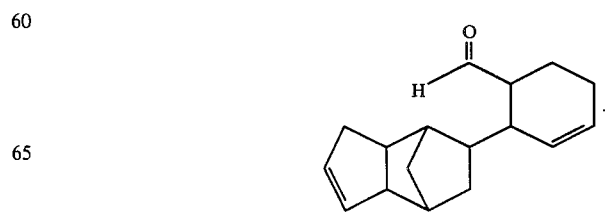

Bulked Fractions 6–10 of the second distillation have a woody, fruity, pineapple-like aroma with woody, leathery and seashore-like topnotes.

EXAMPLE IV

The following compositions are prepared:

| Ingredients | Parts by Weight | | |
|---|---|---|---|
| | IV (A) | IV (B) | IV (C) |
| Linalyl Acetate | 135 | 135 | 135 |
| Bergamot Oil | 275 | 275 | 275 |
| Citronellol | 135 | 135 | 135 |
| Lavandulol | 135 | 135 | 135 |
| Portugal Oil | 135 | 135 | 135 |
| Neroli Oil | 40.5 | 40.5 | 40.5 |
| Jasmin Oil | 20.5 | 20.5 | 20.5 |
| Jasmin Absolute | 20.5 | 20.5 | 20.5 |
| Neroliol, Bigarade | 28.0 | 28.0 | 28.0 |
| Rosemary Oil | 28.0 | 28.0 | 28.0 |
| 4-(4,8-dimethyl-3,7-nonadienyl) pyridine prepared according to Example II of U.S. Pat. No. 3,669,908 | 13.5 | 13.5 | 13.5 |
| Rose Absolute | 13.5 | 13.5 | 13.5 |
| Hydroxy Citronellol | 13.5 | 13.5 | 13.5 |
| Cyclopentadecanolide | 7.0 | 7.0 | 7.0 |
| Bulked Fractions 5–7 of the second distillation of Example I, supra containing the compounds having the structures: 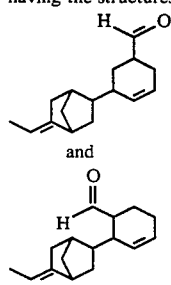 and | 10.0 | 0.0 | 0.0 |
| Bulked Fractions 5–10 of the second distillation of Example II containing the compounds having the structures: 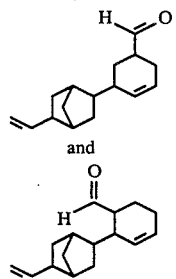 and | 0.0 | 10.0 | 0.0 |
| Bulked Fractions 6–10 of Example III, supra containing the compounds having the structures: 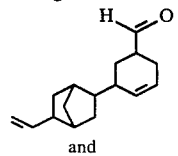 and 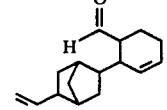 | 0.0 | 0.0 | 10.0 |

The foregoing seashore aroma fragrance is greatly enhanced by the use of the composition of matter containing compounds having the structures:

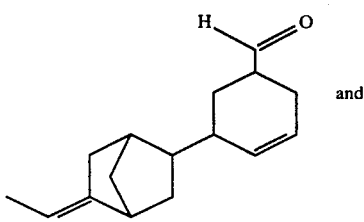

in that, the resulting mixture has earthy undertones and mossy topnotes and an enhanced seashore aroma which is very "natural-like". Accordingly, the perfume composition of Example IV(A) can be described as "seashore-like" with earthy undertones and mossy topnotes.

The mixture of compounds having the structures:

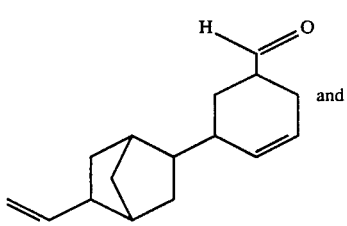

bulked Fractions 5–10 produced according to Example II imparts to this seashore aroma, an excellent green and woody undertones with sweaty and animalic topnotes. Accordingly, the resulting perfume composition of Example IV(B) can be described as a "pleasant, aesthetically pleasing and intense seashore aroma with green and woody undertones and sweaty and animalic topnotes".

The perfume composition of Example IV(C) as a result of addition thereto of the mixture of compounds having the structures:

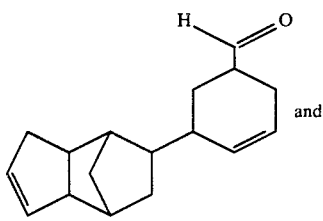

and

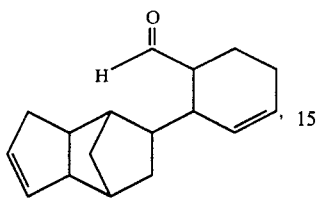

bulked Fractions 6-10 of the distillation product of the reaction product of Example III has imparted to it excellent woody, fruity and pineapple undertones with woody, leathery and "natural-like" seashore topnotes. Accordingly, the aroma of the perfume composition of Example IV(C) can be described as "aesthetically pleasing seashore-like with woody, fruity and pineapple-like undertones and woody, leathery, natural seashore-like topnotes".

EXAMPLE V

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| A mixture of compounds having the structures:<br>[structure]<br>and<br>[structure]<br>bulked Fractions 5-7 of the second distillation of Example I, supra | An earthy, seashore aroma with mossy topnotes. |
| A mixture of compounds having the structures:<br>[structure]<br>and<br>[structure]<br>bulked Fractions 5-10 of the second distillation of Example II, supra. | |
| A mixture of compounds having the structures:<br>[structure]<br>and<br>[structure]<br>bulk distillation Fractions 6-10 of Example III. | A woody, fruity, pineapple-like aroma with woody, leathery and seashore-like topnotes. |
| Perfume composition of Example IV(A) | Seashore-like with earthy undertones and mossy topnotes. |
| Perfume composition of Example IV(B) | Pleasant, aesthetically pleasing and intense seashore aroma with green and woody undertones and sweaty and animalic topnotes. |
| Perfume composition of Example IV(C) | Aesthetically pleasing seashore-like with woody, fruity and pineapple-like undertones and woody, leathery natural seashore-like topnotes. |

EXAMPLE VI

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table II of Example V, are prepared containing 0.10%, 0.15%, 0.20%, 0.25%, 0.30% and 0.35% of the substance set forth in Table II of Example V. They are prepared by adding and homogeneously mixing the appropriate quantity of substance set forth in Table II of Example V in the liquid detergent. The detergents all possess excellent aromas as set forth in Table II of Example V, the intensity increasing with greater concentrations of substance as set forth in Table II of Example V.

EXAMPLE VII

PREPARATION OF COLOGNES AND HANDKERCHIEF PERFUMES

Compositions as set forth in Table II of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example V are imparted to the colognes and to the handkerchief perfumes at all levels indicated.

EXAMPLE VIII

PREPARATION OF SOAP COMPOSITIONS

One hundred grams of soap chips (per sample) (IVORY ®, produced by the Procter & Gamble Company of Cincinnati, Ohio), are each mixed with one gram samples of substances as set forth in Table II of Example V until homogeneous compositions are obtained in each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example V.

EXAMPLE IX

PREPARATION OF SOLID DETERGENT COMPOSITIONS

Detergents are prepared using the following ingredients according to Example I of Canadian Pat. No. 1,007,948 (incorporated by reference herein):

| Ingredient | Percent By Weight |
|---|---|
| Neodol ® 45-11 (a $C_{15}$—$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example V. Each of the detergent samples has an excellent aroma as indicated in Table II of Example V.

EXAMPLE X

Utilizing the procedure of Example I at column 15 of U.S. Pat. No. 3,632,396 (the disclosure of which is incorporated herein by reference), nonwoven cloth substrates useful as dryer-added fabric softening articles of manufacture are prepared wherein the substrate, the substrate coating, the outer coating the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table II of Example V.

Fabric softening compositions prepared according to Example I at column 15 of U.S. Pat. No. 3,632,396 having aroma characteristics as set forth in Table II of Example V, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example V is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table II of Example V, supra.

EXAMPLE XI

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol, 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table II of Example V, supra | |

The perfuming substances as set forth in Table II of Example V add aroma characteristics as set forth in Table II of Example V which are rather intense and aesthetically pleasing to the users of the soft-feel, good-hold pump hair sprays.

EXAMPLE XII

CONDITIONING SHAMPOOS

Monamid CMA (prepared by the Mono Industries Company) (3.0 weight percent) is melted with 2.0 weight percent coconut fatty acid (prepared by Procter & Gamble Company of Cincinnati, Ohio); 1.0 weight percent ethylene glycol disterate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT ® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 disterate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table II of Example V is added to the mixture. The resulting mixture is cooled to 40° C. and blending is carried out for an additional one hour in each case. At the end of this blending period, the resulting material has a pleasant fragrance as indicated in Table II of Example V.

EXAMPLE XIII
PERFUMED POLYMERS

Scented polyethylene pellets having a pronounced seashore aroma were prepared as follows:

75 Pounds of polyethylene of a melting point of about 220° F. were heated to about 230° F. in a container of the kind illustrated in FIGS. 1 and 2 of U.S. Pat. No. 3,505,432, the disclosure of which is incorporated by reference herein. 25 Pounds of the seashore formulation of Example IV(A) were then quickly added to the liquified polyethylene, the lid was put in place and the agitating means were actuated. The temperature was maintained at about 225° F. and the mixing was continued for about 5-15 minutes. The valve was then opened to allow flow of the molten polyethylene enriched with the seashore aroma material to exit through the orifices. The liquid falling through the orifices solidified almost instantaneously upon impact with the moving cooled conveyor. Solid polyethylene beads or pellets having a pronounced seashore aroma were thus formed. Analysis demonstrated that the pellets contained about 25% of the seashore aroma of Example VI(A) so that almost no losses of the scenting substance did occur. These pellets may be called master pellets.

50 Pounds of the seashore aroma-containing master pellets were then added to 1000 pounds of the unscented polyethylene powder and the mass was heated to the liquid state. The liquid was molded into thin sheets or films. The thin sheets or films has a pronounced seashore aroma which may be fabricated into garbage bags and the like.

PATENTS INCORPORATED HEREIN BY REFERENCE

The following patens referred to supra, are hereby incorporated herein by reference:
U.S. Pat. No. 3,632,396
U.S. Pat. No. 3,948,818
U.S. Pat. No. 3,505,432
Canadian Pat. No. 1,007,948

What is claimed is:

1. A process for augmenting or enhancing the aroma of a perfume composition comprising the step of adding to said perfume composition, an aroma augmenting or enhancing quantity of a mixture of norbornylbutadiene acrolein adducts defined according to the structures:

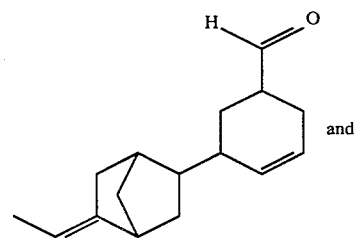

2. A process for augmenting or enhancing the aroma of a solid or liquid anionic, cationic, nonionic or zwitterionic detergent comprising the step of adding to said detergent, an aroma augmenting or enhancing quantity of a mixture of norbornylbutadiene acrolein adducts defined according to the structures:

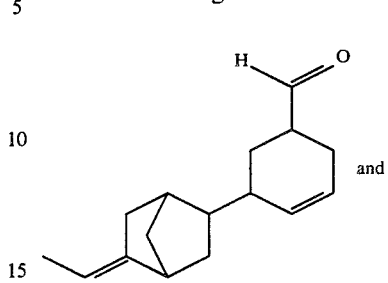

3. A process for augmenting or enhancing the aroma of a perfumed polymer comprising the step of adding to said perfumed polymer, an aroma augmenting or enhancing quantity of a mixture of norbornylbutadiene acrolein adducts defined according to the structures:

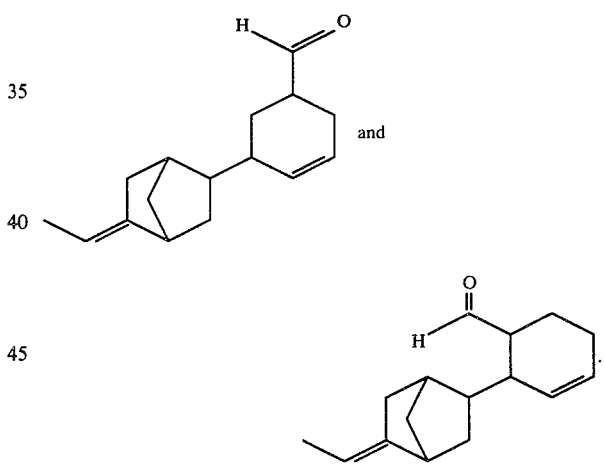

4. A process for augmenting or enhancing the aroma of a fabric softener composition comprising the step of adding to said fabric softener composition, an aroma augmenting or enhancing quantity of a mixture of norbornylbutadiene acrolein adducts defined according to the structures:

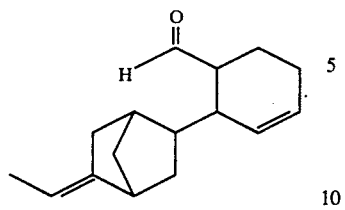

5. A process for augmenting or enhancing the aroma of a perfume composition comprising the step of adding to said perfume composition, an aroma augmenting or enhancing quantity of a mixture of norbornylbutadiene acrolein adducts defined according to the structures:

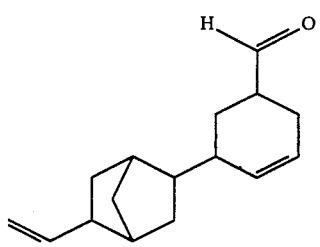

and

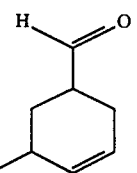

6. A process for augmenting or enhancing the aroma of a solid or liquid anionic, cationic, nonionic or zwitterionic detergent comprising the step of adding to said detergent, an aroma augmenting or enhancing quantity of a mixture of norbornylbutadiene acrolein adducts defined according to the structures:

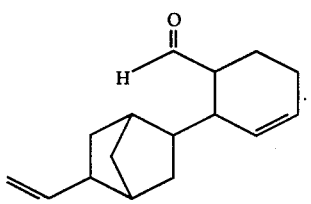

and

7. A process for augmenting or enhancing the aroma of a perfumed polymer comprising the step of adding to said perfumed polymer, an aroma augmenting or enhancing quantity of a miture of norbornylbutadiene acrolein adducts defined according to the structures:

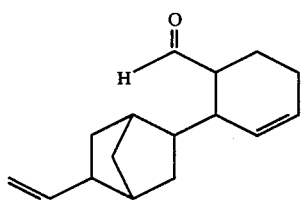

and

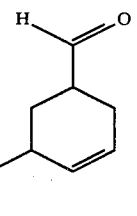

8. A process for augmenting or enhancing the aroma of a fabric softener composition comprising the step of adding to said fabric softener composition, an aroma augmenting or enhancing quantity of a mixture of norbornylbutadiene acrolein adducts defined according to the structures:

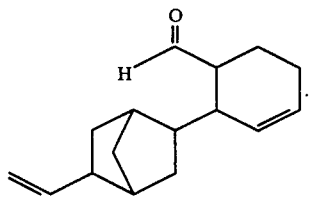

and

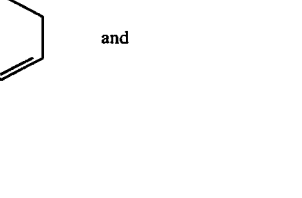

* * * * *